(12) United States Patent
Townsend et al.

(10) Patent No.: US 12,194,163 B2
(45) Date of Patent: Jan. 14, 2025

(54) APPARATUSES AND METHODS TO ATTENUATE VIRUSES

(71) Applicant: Respiratory Health Technologies, Inc., Indianapolis, IN (US)

(72) Inventors: Jackson Alexander Townsend, Zionsville, IN (US); Matthew Raymond Zielinski, Indianapolis, IN (US); Reuben Quincey Zielinski, Fishers, IN (US); Robert Anderson Till, Avon, IN (US)

(73) Assignee: Respiratory Health Technologies, Inc., Indianapolis, IN (US)

( * ) Notice: Subject to any disclaimer, the term of this patent is extended or adjusted under 35 U.S.C. 154(b) by 531 days.

(21) Appl. No.: 17/212,314

(22) Filed: Mar. 25, 2021

(65) Prior Publication Data

US 2021/0299288 A1 Sep. 30, 2021

Related U.S. Application Data

(60) Provisional application No. 63/017,615, filed on Apr. 29, 2020, provisional application No. 62/994,408, filed on Mar. 25, 2020.

(51) Int. Cl.
*A61L 2/00* (2006.01)
*A61L 2/24* (2006.01)
(Continued)

(52) U.S. Cl.
CPC .............. *A61L 2/0023* (2013.01); *A61L 2/24* (2013.01); *A61M 16/0045* (2013.01);
(Continued)

(58) Field of Classification Search
CPC ...... A61L 2/0023; A61L 2/24; A61L 2202/11; A61L 2202/14; A61L 2202/15;
(Continued)

(56) References Cited

U.S. PATENT DOCUMENTS

| 603,021 A | 4/1898 | Dight |
| 2,241,356 A | 5/1941 | Magee |

(Continued)

FOREIGN PATENT DOCUMENTS

| CN | 105498066 A | * | 4/2016 |
| EP | 0884062 A1 | * | 12/1998 |

(Continued)

*Primary Examiner* — Michael R Reid
*Assistant Examiner* — Tina Zhang
(74) *Attorney, Agent, or Firm* — Taylor IP, P.C.

(57) ABSTRACT

A virus attenuator includes: a housing defining an interior and having at least one intake port fluidly coupled to the interior and a gas ejection nozzle fluidly coupled to the interior, the gas ejection nozzle being configured to couple to a mask; and at least one heater disposed in the interior between the at least one intake port and the gas ejection nozzle such that at least some gas brought into the interior through the at least one gas intake port contacts the at least one heater. The at least one heater is configured to heat contacting gas to a virus attenuating temperature before the contacting gas exits the interior through the gas ejection nozzle.

18 Claims, 21 Drawing Sheets

(51) Int. Cl.
*A61M 16/00* (2006.01)
*A61M 16/06* (2006.01)
*A61M 16/10* (2006.01)

(52) U.S. Cl.
CPC .......... *A61M 16/024* (2017.08); *A61M 16/06* (2013.01); *A61M 16/1075* (2013.01); *A61L 2202/11* (2013.01); *A61L 2202/14* (2013.01); *A61L 2202/15* (2013.01); *A61M 2205/3327* (2013.01); *A61M 2205/3344* (2013.01); *A61M 2205/3365* (2013.01); *A61M 2205/3368* (2013.01); *A61M 2205/3553* (2013.01); *A61M 2205/3584* (2013.01); *A61M 2205/502* (2013.01); *A61M 2205/6063* (2013.01)

(58) Field of Classification Search
CPC ... A61L 9/16; A61M 16/0045; A61M 16/024; A61M 16/06; A61M 16/1075; A61M 2205/3327; A61M 2205/3344; A61M 2205/3365; A61M 2205/3368; A61M 2205/3553; A61M 2205/3584; A61M 2205/502; A61M 2205/6063; A61M 16/08; A61M 16/0066; A61M 16/0816; A61M 16/161; A61M 2016/0027; A61M 2202/0225; A61M 2202/206; A61M 2205/3592; A61M 2205/505; A61M 2205/52; A61M 2205/583; A61M 2230/432

See application file for complete search history.

(56) References Cited

U.S. PATENT DOCUMENTS

| | | | |
|---|---|---|---|
| 2,309,846 A | 2/1943 | Holm | |
| 2,784,714 A | 3/1957 | Pitzipio | |
| 3,115,134 A | 12/1963 | Schmahl | |
| 3,139,885 A | 7/1964 | Hirtz et al. | |
| 3,249,108 A | 5/1966 | Terman | |
| 3,820,540 A | 6/1974 | Hirtz et al. | |
| 4,601,287 A | 7/1986 | Royce, Jr. | |
| 4,620,537 A | 11/1986 | Brown | |
| 4,793,343 A | 12/1988 | Cummins, Jr. et al. | |
| 4,905,686 A * | 3/1990 | Adams | A61M 16/1075 128/207.12 |
| 5,038,769 A * | 8/1991 | Krauser | A61M 15/00 128/203.27 |
| 5,511,541 A | 4/1996 | Dearstine | |
| 6,470,885 B1 * | 10/2002 | Blue | A61M 16/0677 128/204.24 |
| 6,672,129 B1 * | 1/2004 | Frederickson | A61M 15/025 73/1.06 |
| 9,775,740 B2 * | 10/2017 | Bly | A61F 7/0085 |
| 10,772,371 B1 | 9/2020 | Sabin | |
| 10,905,585 B1 | 2/2021 | Sabin | |
| 2003/0065274 A1 * | 4/2003 | Mault | A61B 5/087 600/531 |
| 2005/0150501 A1 * | 7/2005 | Opitz | A61M 16/108 128/207.18 |
| 2005/0268911 A1 * | 12/2005 | Cross | A61M 11/002 128/203.26 |
| 2009/0025564 A1 * | 1/2009 | Kuwabara | F04B 39/0061 181/269 |
| 2011/0162647 A1 * | 7/2011 | Huby | A61M 16/16 128/203.14 |
| 2016/0334119 A1 * | 11/2016 | Cameron | A24F 40/30 |
| 2017/0173285 A1 * | 6/2017 | Culp, Jr. | A61M 16/06 |
| 2020/0297960 A1 * | 9/2020 | O'Donnell | A61M 16/0063 |

FOREIGN PATENT DOCUMENTS

| | | |
|---|---|---|
| GB | 2 277 689 A | 11/1994 |
| GB | 2 440 722 A | 2/2008 |

* cited by examiner

APPARATUSES AND METHODS TO ATTENUATE VIRUSES

CROSS REFERENCE TO RELATED APPLICATIONS

This is a non-provisional application based upon U.S. provisional patent application Ser. No. 63/017,615, entitled "APPARATUSES AND METHODS TO ATTENUATE VIRUSES", filed Apr. 29, 2020, and U.S. provisional patent application Ser. No. 62/994,408, entitled "APPARATUSES AND METHODS TO ATTENUATE VIRUSES", filed Mar. 25, 2020, which are both incorporated herein by reference.

BACKGROUND OF THE INVENTION

1. Field of the Invention

The present invention relates to devices and methods that can be used to attenuate viruses, and, more particularly, to devices and methods that can be used to attenuate viruses using heat.

2. Description of the Related Art

According to the Centers for Disease Control and Prevention (CDC), many viruses can cause produce standard common cold symptoms such as rhinitis and congestion, but rhinoviruses are the most common and hence, are most often associated with the common cold. These rhinoviruses are spread through respiratory droplets and close personal contact. Accordingly, it has been generally understood because of the prevalence of these rhinoviruses, there is no cure for the common cold and society has primarily focused on prevention methods for common cold reduction. These prevention methods include washing hands thoroughly with soap and water for as long as 20 seconds, disinfecting surfaces, avoiding people with colds, and avoid touching eyes, nose, and mouth with unwashed hands. Because the virus incubates within the superficial epithelium of the mucosal surfaces of the oropharynx and nasopharynx it is easily transmitted.

By current estimates, in the course of a year, people in the U.S. suffer over 1 billion colds. Most colds occur during the fall and winter months. Beginning in late August or early September, the rate of colds increases slowly for a few weeks and remains high until March or April, when it begins to decline. The seasonal variation may relate to the opening of schools and to cold weather, which prompt people to spend more time indoors and increase the chances that viruses will spread between personal contacts. During these cold seasons, according to some estimates, over $40 Billion is spent in the U.S. on cold remedies.

Children usually have about 6 to 10 colds per year. One important reason why colds are so common in children is because they are often in close contact with each other in daycare centers and schools. In families with children in school, the number of colds per child can be as high as 12 per year. Adults average about 2 to 4 colds per year, although the range varies widely. Women, especially those aged 20 to 30 years, have more colds than men, possibly because of their closer contact with children. On average, people older than age 60 have fewer than one cold per year.

Seasonal changes in relative humidity also may affect the prevalence of colds. The most common cold-causing viruses survive better when humidity is low and during the colder months of the year. Cold weather also may make the inside lining of your nose drier and more vulnerable to viral infection. Sneezing, scratchy throat, runny nose are the first signs of a cold, and probably the most common illness known. Although the common cold is usually mild, with symptoms lasting 1 to 2 weeks, it is a leading cause of doctor visits and missed days from school and work. According to the CDC, 22 million school days are lost annually in the United States because of the common cold.

It is common knowledge that many people, during the warmer, more humid months, begin to feel the symptoms of the common cold as they enter and exit air-conditioned premises and offices. Many times, people complain they get scratchy and sore throats just from spending time in their air-conditioned cars. Sleeping under a ceiling fan or next to an open window with the night air dropping often leads to common cold symptoms.

The human rhinovirus is the most common cause of the common cold. It replicates in the superficial mucosa of the nose and throat. The inflammatory response to the virus causes the symptoms, and Tyrell and Rodgers discovered that the virus replicates optimally at 33 degrees Celsius (91.4 degrees Fahrenheit). The replication of the virus is impeded by increased temperatures. The decrease in viral replication appears to be directly correlated to an increase in temperature.

The human rhinovirus was discovered to be the causative agent of the respiratory illness moving through the Baltimore Hospitals and John Hopkin's Hospital in the 1950's. Additional studies isolated the human rhinovirus from monkeys and horses in 1956 and concluded it produced an upper airway infection leading to malaise, coryza (inflammation of the nose), and a mild sore throat. Rhinoviruses are the most commonly recovered agents from people with mild upper respiratory illnesses. They are usually isolated from nasopharyngeal secretions but may also be found in throat and oral secretion. Replication is limited to the surface epithelium of the nasal mucosa.

It is currently believed that the two most common symptoms, rhinorrhea and nasal obstruction, are a result of the increased neutrophilic inflammatory response to the virus. There is an increased permeability in the mucous membranes of the nasopharynx in response to the virus. This leads to an increase in the production and excretion of mucus. Many believe that the cough that often develops later in the illness results from the excess drainage of mucus into the posterior pharynx.

There are some lower respiratory symptoms seen in asthma patients but the mechanism behind the symptoms is still debated. Additionally, scientists still debate whether the virus can infect cells of the lower respiratory track.

There are many studies that indicate that the replication of the virus is impeded by supra-optimal (warmer) temperatures. The graph of FIG. 19 shows decreased viral replication at 39 degrees Celsius (102.2 degrees Fahrenheit). The graph of FIG. 20 is from a different study and shows the decreased viral growth at higher temperatures. The viral load was measured after a 20 min exposure to 37°, 43°, and 45° C. temperatures.

In more recent studies, it has been observed that SARS-CoV-2, which causes COVID-19, has had a greater impact on countries with colder climates. A study published on Mar. 9, 2020, demonstrated that even when controlling for population density, colder climates have a statistically significant increased number of COVID-19 cases. The correlation between warmer temperatures and a decrease in the quantity and severity of viral cases is observed in other viral families, including the common cold. For the past 30 years, extensive research has been conducted demonstrating that heat can stop the proliferation of viruses. Put simply, the physiologic response to elevate body temperature in the event of an infection is believed to be a natural defense mechanism to limit the replication of the infecting pathogen. The graph of FIG. 21 illustrates the 24-hour reduction of viral proliferation of the SARS Coronavirus (also known as SARS-CoV or SARS-CoV-1) in response to an elevated temperature.

What is needed in the art is a new technique and associated apparatus to reduce the virus growth and addresses one or more of the shortcomings of the treatments for the common cold, SARS, COVID-19, and any other viruses that can be attenuated with higher temperatures according to the prior art.

SUMMARY OF THE INVENTION

The present invention provides an apparatus and method having features that provide a better, more consistent treatment for reducing viruses as well as a simple way to measure the treatment time.

In some exemplary embodiments provided according to the present invention, a virus attenuator includes at least a first heater board, a control board, and a fan actuated gas pressure producer. The heater board includes a plurality of surface mount resistors and gas through-ports. The fan actuated gas producer is directly and securely fastened in between the heater board and control board. The control board includes a microcontroller, indicator LED lights, switches, and driver circuitry to power the fan actuated gas producer and heater board.

In some exemplary embodiments provided according to the present invention, a virus attenuator includes a housing and a distal sensor board. The housing defines a heated gas producing chamber that tapers to a standard rebreathing mask input port. The sensor board defines a temperature sensor, a humidity sensor, a pressure sensor, and a carbon dioxide sensor.

In some exemplary embodiments provided according to the present invention, a virus attenuator includes a housing, tapered on both distal and proximal ends, which can be inserted into a ventilator breathing circuit or continuous positive airway pressure (CPAP) breathing circuit. The virus attenuator includes a control board, a heater board, and a sensor board.

In some embodiments, a feature is added to the control board to allow wireless data transmission to record the virus attenuator sensor responses. In some embodiments, a software application is configured to receive the wireless transmission of sensor data and allow user interaction with the virus attenuator operation efficiency.

In some exemplary embodiments provided according to the present invention, a virus attenuator includes: a housing defining an interior and having at least one intake port fluidly coupled to the interior and a gas ejection nozzle fluidly coupled to the interior, the gas ejection nozzle being configured to couple to a mask; and at least one heater disposed in the interior between the at least one intake port and the gas ejection nozzle such that at least some gas brought into the interior through the at least one gas intake port contacts the at least one heater. The at least one heater is configured to heat contacting gas to a virus attenuating temperature before the contacting gas exits the interior through the gas ejection nozzle.

In some exemplary embodiments provided according to the present invention, a breathing system includes a mask having a coupler and a virus attenuator coupled to the mask. The virus attenuator includes: a housing defining an interior and having at least one intake port fluidly coupled to the interior and a gas ejection nozzle fluidly coupled to the interior and coupled to the coupler of the mask; and at least one heater disposed in the interior between the at least one intake port and the gas ejection nozzle such that at least some gas brought into the interior through the at least one gas intake port contacts the at least one heater. The at least one heater is configured to heat contacting gas to a virus attenuating temperature before the contacting gas exits the interior through the gas ejection nozzle into the mask.

In some exemplary embodiments, a method of treating a patient infected with a respiratory virus is provided. The method includes: fitting a breathing device to the patient so the patient breathes in gas through the breathing device; producing heated gas that is at a virus attenuating temperature using a virus attenuator, the virus attenuator including: a housing defining an interior and having at least one intake port fluidly coupled to the interior and a gas ejection nozzle fluidly coupled to the interior, the gas ejection nozzle being coupled to a coupler of the breathing device; and at least one heater disposed in the interior between the at least one intake port and the gas ejection nozzle such that at least some gas brought into the interior through the at least one gas intake port contacts the at least one heater, the at least one heater heating contacting gas to the virus attenuating temperature to produce the heated gas; and providing the heated gas to the patient through the breathing device.

An advantage of the present invention is that the duration and severity of viral infection, such as infection with SARS-CoV, can be limited by producing a localized hyperthermic environment using the viral attenuator provided according to the present invention.

Another advantage is the virus attenuator can be coupled to many different types of masks to provide breathing systems that can provide other healthcare support functions, such as ventilation.

Yet another advantage is the virus attenuator can be monitored remotely to allow a healthcare provider to monitor parameters of operation without being in close proximity to a patient using the virus attenuator, reducing the risk of an infection passing between the healthcare provider and the patient.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
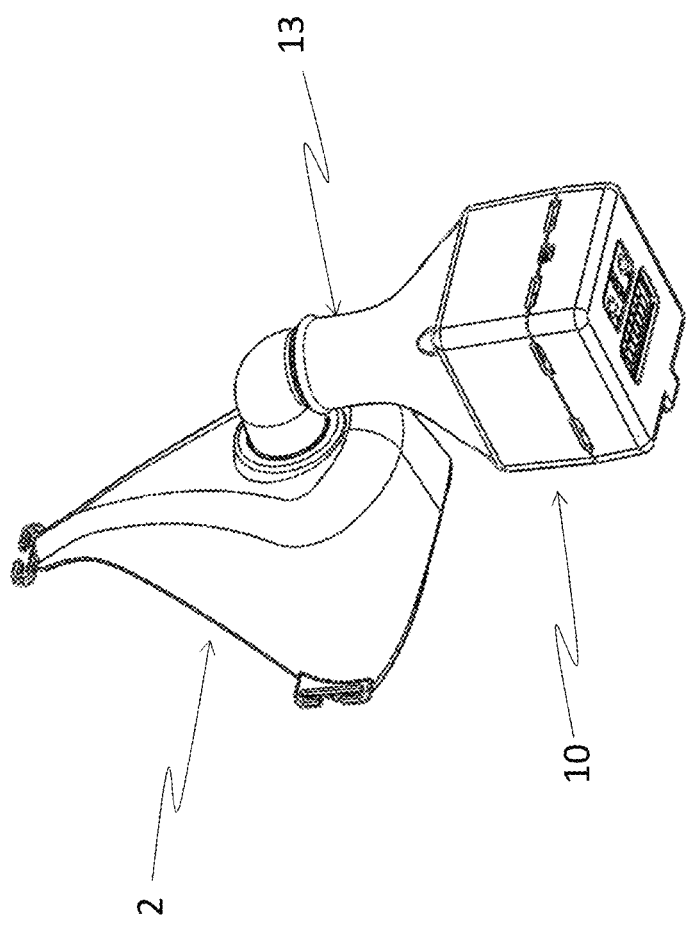
FIG. 1 shows a perspective view of a virus attenuator and associated breathing mask which the virus attenuator could be attached to while in use.

For the purposes of promoting an understanding of the principles of the invention, reference is made to selected embodiments illustrated in the drawings and specific language will be used to describe the same. It will nevertheless be understood that no limitation of the scope of the invention is thereby intended; any alterations and further modifications of the described or illustrated embodiments, and any further applications of the principles of the invention as illustrated herein are contemplated as would normally occur to one skilled in the art to which the invention relates. At least one embodiment of the invention is shown in great detail, although it will be apparent to those skilled in the relevant art that some features or some combinations of features may not be shown for the sake of clarity.

Any reference to "invention" within this document is a reference to an embodiment of a family of inventions, with no single embodiment including features that are necessarily included in all embodiments, unless otherwise stated. Furthermore, although there may be references to "advantages" provided by some embodiments of the present invention, other embodiments may not include those same advantages, or may include different advantages. Any advantages described herein are not to be construed as limiting to any of the claims.

Specific quantities (spatial dimensions, temperatures, pressures, times, force, resistance, current, voltage, concentrations, wavelengths, frequencies, heat transfer coefficients, dimensionless parameters, etc.) may be used explicitly or implicitly herein, such specific quantities are presented as examples only and are approximate values unless otherwise indicated. Discussions pertaining to specific compositions of matter, if present, are presented as examples only and do not limit the applicability of other compositions of matter, especially other compositions of matter with similar properties, unless otherwise indicated.

Figure 2:
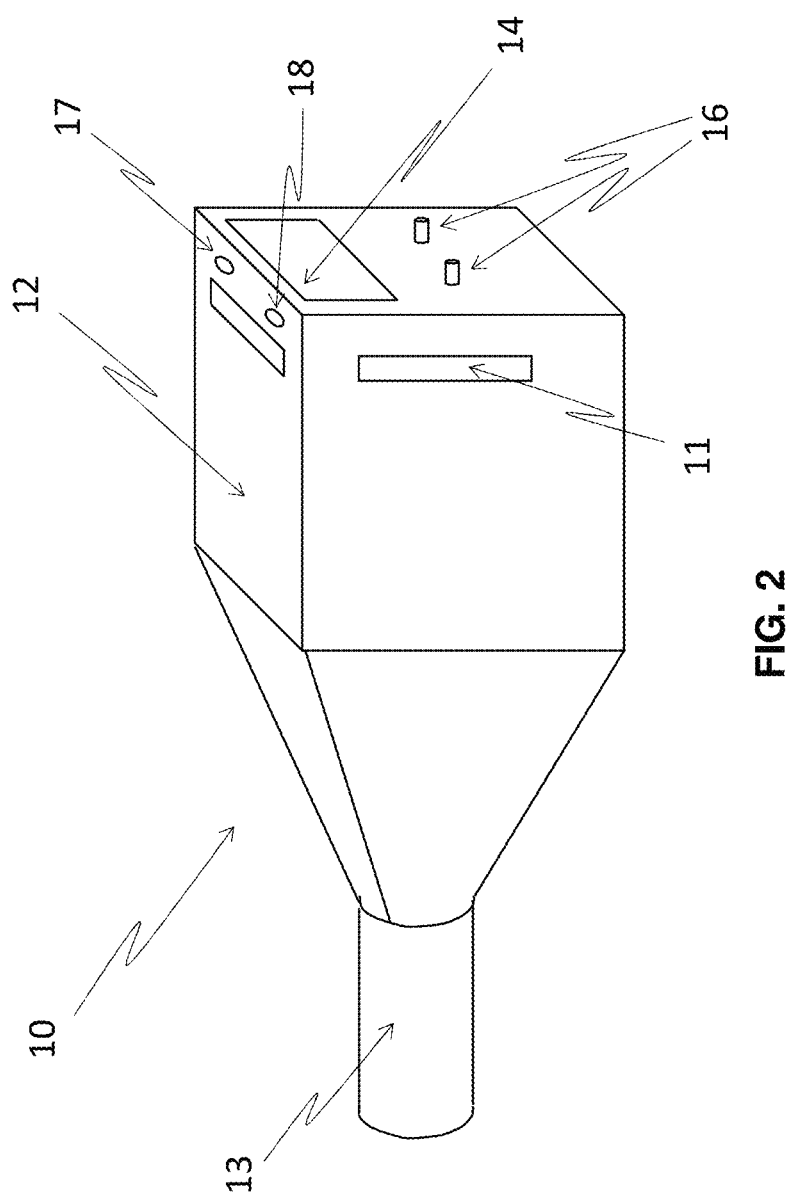
FIG. 2 shows a front and side perspective view of an exemplary embodiment of a virus attenuator housing provided according to the present invention.
Figure 3:
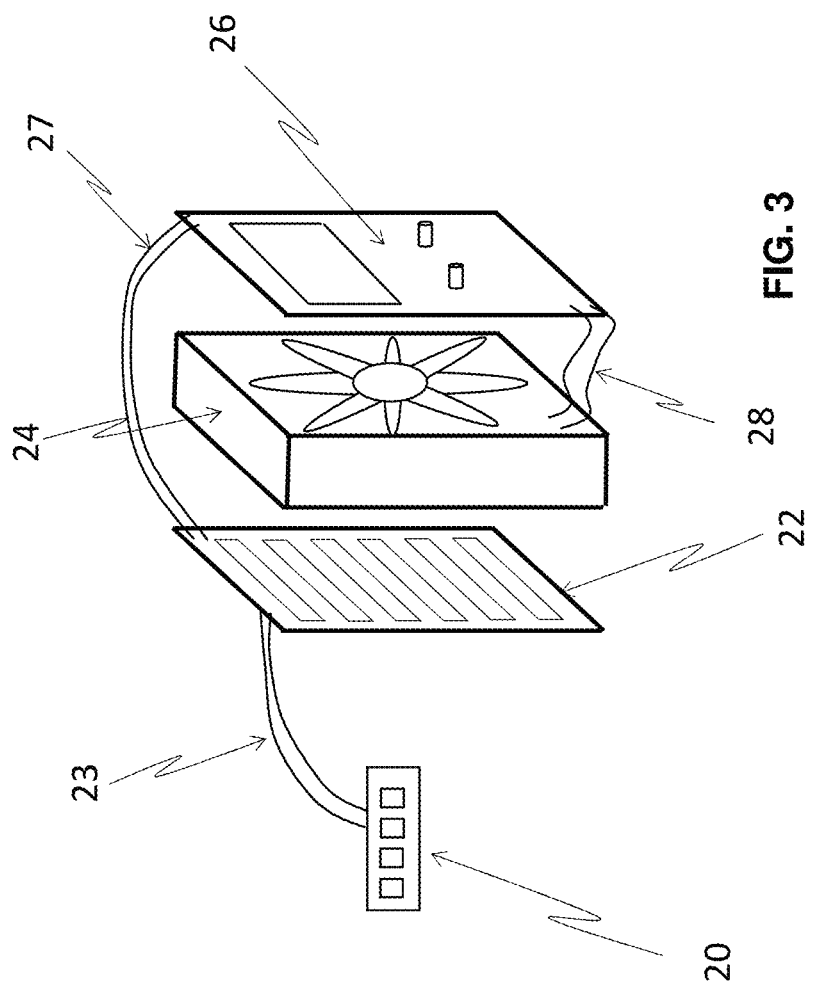
FIG. 3 shows a side view of components that may be disposed in the housing of the virus attenuator of FIG. 1 stacked in planar fashion.

FIG. 1 shows a perspective side view of an exemplary embodiment of a virus attenuator 10 coupled together with a mating rebreathing mask 2 to form a breathing system. Heated gas, such as atmospheric air, pure oxygen, or a high-oxygen gas blend, from virus attenuator 10 is supplied to mask 2, which may then be presented to the nasopharynx of a patient wearing mask 2 to warm the upper respiratory tract (URT). Providing heated gas to the URT of the patient can increase the local temperature within the URT, where a respiratory virus may be replicating, in order to make the URT a less hospitable environment for the virus and slow the rate of viral replication. FIG. 2 shows a perspective view of an embodiment of a virus attenuator 10. FIG. 3 shows a sideway view of the stacked components of the virus attenuator 10. With reference to FIGS. 1-3 the virus attenuator 10 includes housing 12 and gas ejection nozzle 13 coupled to coupler 3 of mask 2. Housing 12 has an interior and includes at least one intake port, illustrated as multiple intake ports 11, fluidly coupled to the interior and indicator lamps configured to indicate therapeutic range achievement, illustrated in the form of green LED indicator 17 and red LED indicator 18. Housing 12 has features allowing display 14 to be viewed and control buttons 16 to protrude through housing 12 for actuation purposes. Display 14 may include a light-emitting diode (LED) display or a liquid-crystal display (LCD). Housing 12 may be fabricated from rigid elastomer (plastic) with inside alignment features configured to allow control board 26, gas pressure producing fan 24, which may also be referred to as an "gas pressure producing fan" or just a "fan," and at least one heater, illustrated in the form of heater board 22, to be mounted planar within housing 12. Exemplary materials of housing 12 include, but are not limited to, high temperature polymeric materials such as polycarbonate, acrylonitrile butadiene styrene (ABS), poly(methyl methacrylate) (also known as "acrylic"), and/or polyetherimide (PEI), such as a PEI sold under the tradename ULTEM®. Ejection nozzle 13 being a part of housing 12 channels gas flow around sensor board 20. Ejection nozzle 13 is configured to couple, such as by a friction fit, to a mask, such as a rebreathing mask, and has an outside diameter that allows such coupling. It is generally understood by those skilled in the art of rebreathing masks that ejection nozzle 13 can be fabricated in any diameter to fit any number of masks available. In some embodiments, the ejection nozzle outside diameter is approximately 0.7 inches, which allows fitment into most generally available rebreathing masks. As illustrated, ejection nozzle 13 may be part of a tapered exhaust output of housing 12 that is configured to fit a mask, such as rebreathing mask 2. Rebreathing mask 2 may have a diameter of 0.65 inches to 0.75 inches. Alternatively, or in addition, tapered exhaust output may be configured to fit a plurality of adapters configured to couple tapered exhaust output to a rebreathing mask, so tapered exhaust output can couple to a large variety of rebreathing masks.

In some embodiments, control board 26 is electrically connected to gas pressure producing fan 24 via fan control wiring 28, and to heater board 22 through heater board wiring 27. Heater board wiring 27 contains additional wiring for sensor board buss 23. Sensor board 20 is electrically connected through sensor board buss 23.

Figure 4:
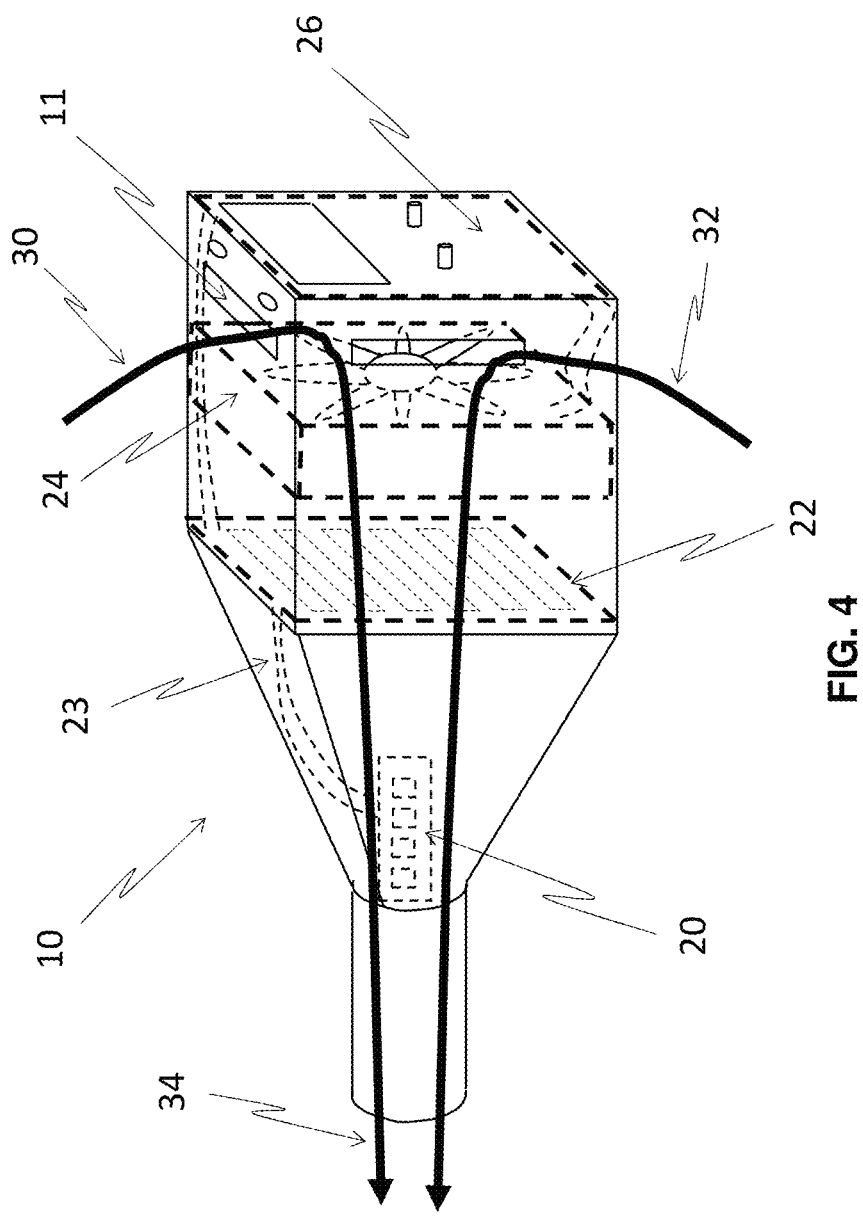
FIG. 4 shows a side cutaway view of the stacked components inside the housing of the virus attenuator of FIG. 1.

FIG. 4 shows a cutaway perspective view of the virus attenuator 10 with gas flow paths 30 and 32 respectively. Gas flow paths 30 and 32 are defined by intake ports 11 being on the intake side of gas pressure producing fan 24 and the backside of control board 26. It is generally understood that there can be a plurality of intake ports 11 about the sides of housing 12. Gas flow paths 30 and 32 combine in the interior to generate accumulated gas flow 34 which exits ejection nozzle 13 to, for example, coupled mask 2. In this respect, heater board 22 is disposed in the interior of housing 12 between intake ports 11 and gas ejection nozzle 13 such that at least some of the gas brought into the interior of housing 12 through intake ports 11 contacts heater board 22 and heater board 22 heats the contacting gas to a virus attenuating temperature before the contacting gas exits the interior through gas ejection nozzle 13. Fan 24 may be directed at heater board 22 to produce the gas flow paths 30, 32, which may also be referred to as a "gas flow", directed at heater board 22.

Figure 5:
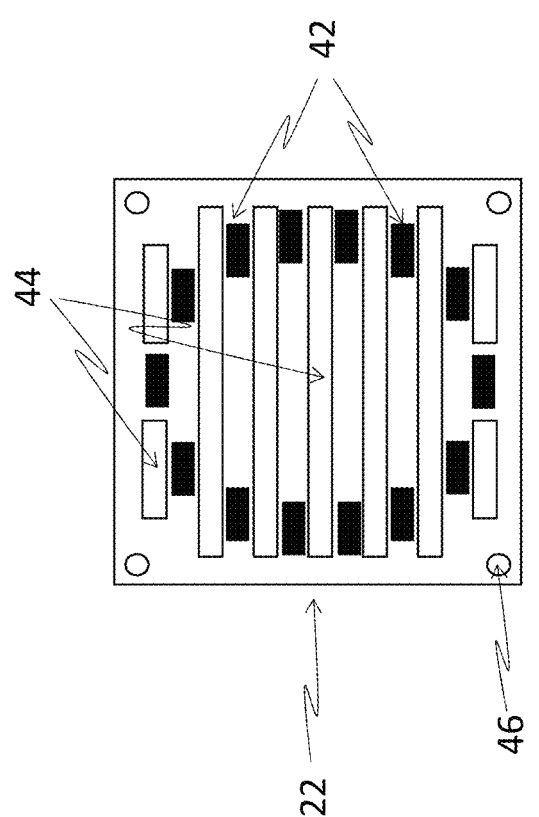
FIG. 5 shows a front view of the virus attenuator heater board of FIG. 3.
Figure 6:
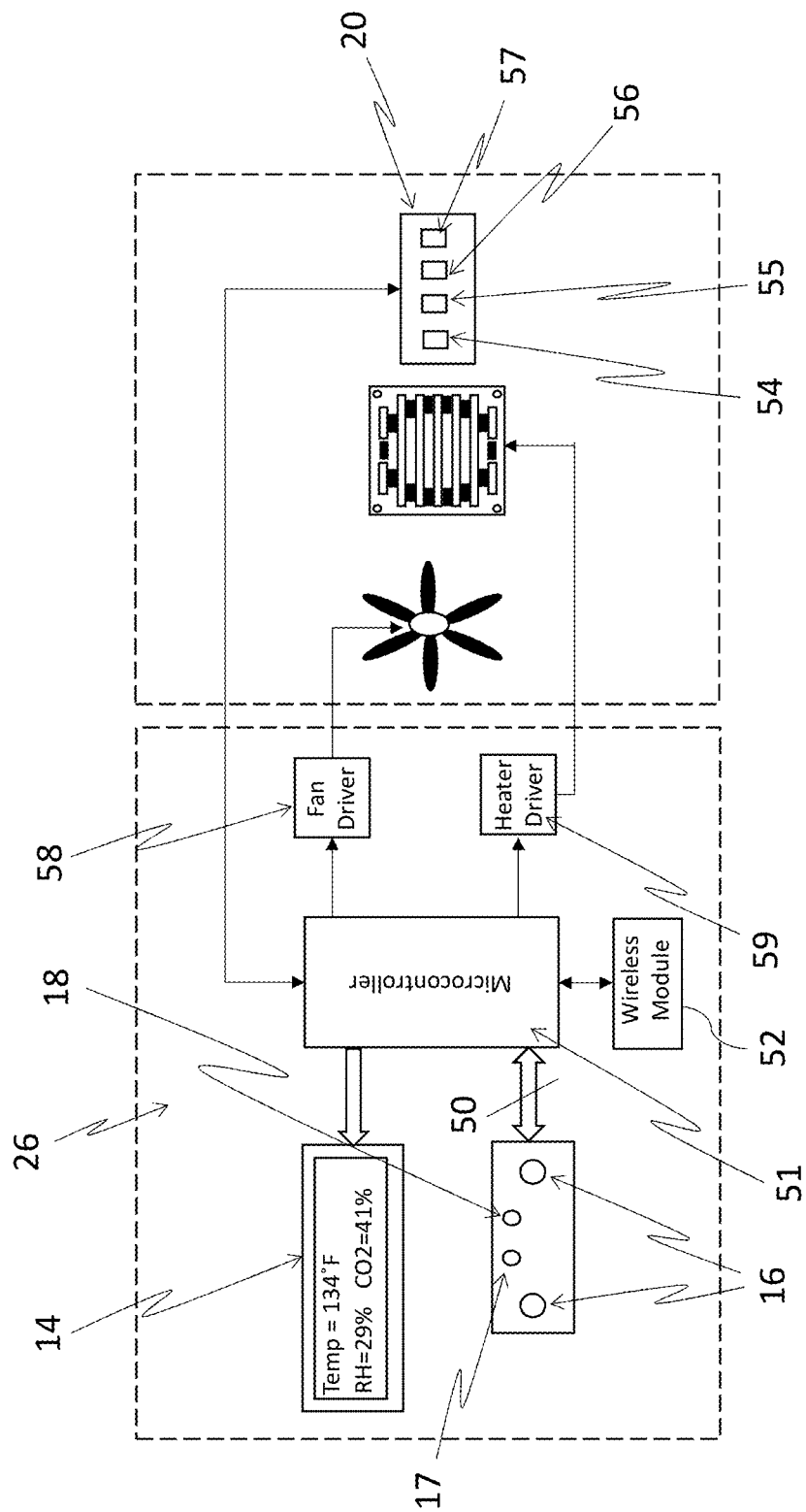
FIG. 6 shows a block diagram of an exemplary embodiment of a control scheme of the virus attenuator of FIG. 4.

Now referring to FIG. 5 and FIG. 6, it is illustrated how heater board 22 may comprise surface mount resistors 42, gas flow thru ports (slots) 44, and heater mounting holes 46. Heater mounting holes 46 are aligned with similar mounting holes on control board 26 and gas pressure producing fan 24. Sensor board 20 may comprise temperature sensor 54, humidity sensor 55, pressure sensor 56, and carbon dioxide sensor 57. Each of the sensors 54, 55, 56, 57 may be operably coupled to microcontroller 51. The relative humidity, gas pressure, and carbon dioxide may be measured using inter-integrated circuit (I2C) signals, serial peripheral interface (SPI) signals, and/or analog signals.

As best shown in FIG. 4, gas flow paths 30 and 32 are created by gas pressure producing fan 24 impinging gas onto heater board 22 and resistors 42 mounted to a surface of heater board 22, which then passes thru slots 44 formed in the surface of heater board 22 and passes over sensor board 20. In some embodiments, heater board 22 is configured to convert between 10 watts and 100 watts of power into heat. Heater board 22 may include at least 7, but no more than 50, resistors 42 each having a power dissipation of 1.5-2 watts per resistor 42. Slots 44 may be disposed alternately between resistors 42, as illustrated in FIGS. 5-6. In some embodiments, heater board 22 includes a plurality of serpentine conductive circuit traces that each have a trace width between 4 mm and 15 mm and a total ohmic value of 0.5 ohms to 10 ohms.

FIG. 6 depicts control board 26 comprising microcontroller 51, display 14, gas pressure producing fan driver 58, which may also be referred to as "fan driver 58," heater board driver 59, which may also be referred to as "heater driver 59," LED indicator lights 17 and 18, and control buttons 16 interfaced electrically to microcontroller 51 via interface buss 50. Microcontroller 51 may be coupled to fan driver 58 and heater driver 59 and configured to control a heater board power supplied to heater board 22 and a fan speed of fan 24 using pulse width modulation.

Figure 7:
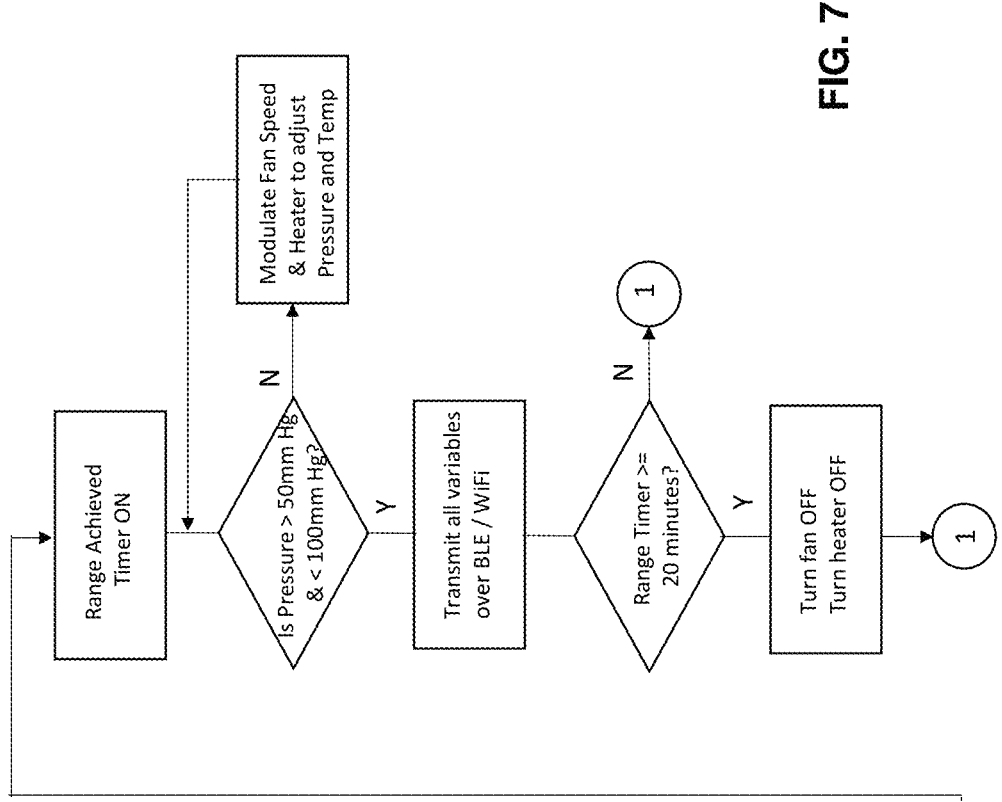
FIG. 7 shows a flowchart illustrating the logic that may be used in the virus attenuator microcontroller of FIG. 4.
Figure 7:
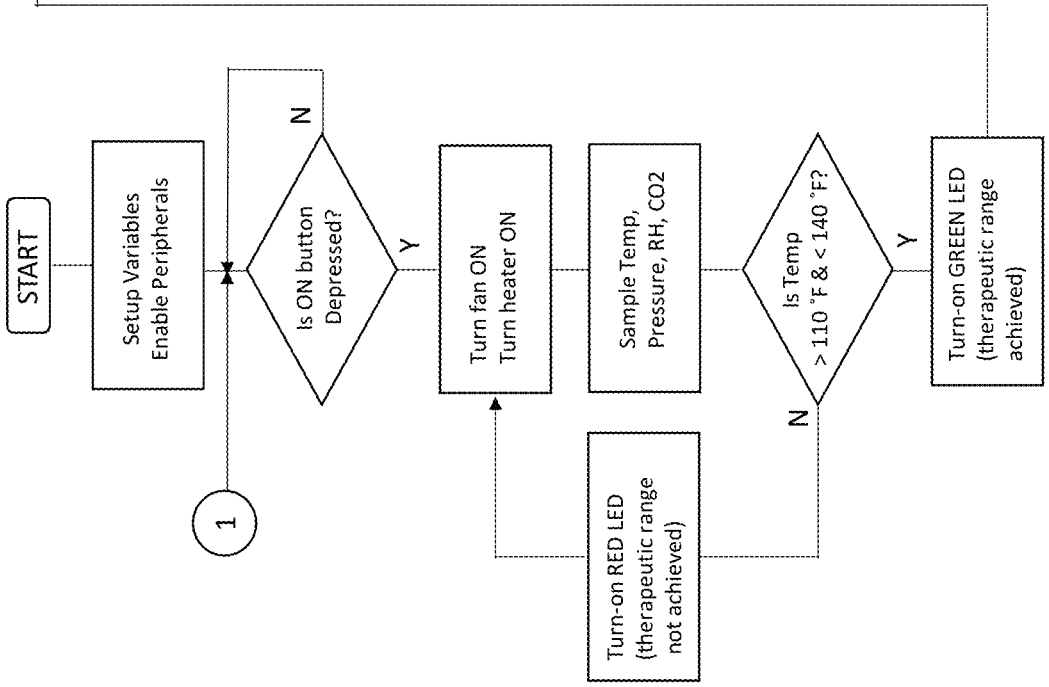

FIG. 7 depicts an exemplary embodiment for a control scheme flowchart for firmware logic used by microcontroller 51 of FIG. 6. The overall control scheme provides software control of gas pressure producing fan 24 and heater board 22 via feedback from sensor board 20 comprising temperature sensor 54, humidity sensor 55, pressure sensor 56, and carbon dioxide sensor 57. Temperature sensor 54 may include, for example, a thermistor in a resistor divider network to measure the heater board temperature and the exhaust gas temperature. The heater board temperature may also be measured with a surface mount negative temperature compensating thermistor. Microcontroller 51 may be configured to determine a heater board temperature, determine an exhaust gas temperature, determine a relative humidity, determine a gas pressure, and/or determine a carbon dioxide content based on received signals from the sensors 54, 55, 56, 57.

The control scheme flowchart in FIG. 7 can control the virus attenuator 10 producing pressurized gas at 80-100 mmHg at a virus attenuating temperature range of 100° F. to 140° F., such as 110° F. to 140° F., for an elapsed time of 20 or more minutes. By way of medical studies, this therapeutic range of temperature and time can reduce the plaque forming units per milliliter of virus greater than 100× (2 log). It is generally understood by those skilled in the art of control systems that these stated target parameters that can modify the pressure, temperatures, and times are user-definable in the control scheme and are in no way limited to the spatial values indicated. Humidity sensor 55 and carbon dioxide sensor 57 can be used to determine end points in the virus treatment therapy. In some embodiments, a humidity and carbon dioxide signature analysis can be acted upon by microcontroller 51 to signify reduction of the rhinovirus, SARS-CoV-1, SARS-CoV-2, the onset of bronchitis, or pneumonia which usually follow the common cold. Fan 24 may be configured to produce a static pressure of 10 mmHg to 150 mmHg. While the virus attenuating temperature range is described as being 100° F. to 140° F., it should be appreciated that heater 22 may be configured to heat to a higher temperature than 140° F. to, for example, quickly heat contacting gas to the virus attenuating temperature.

Figure 8:
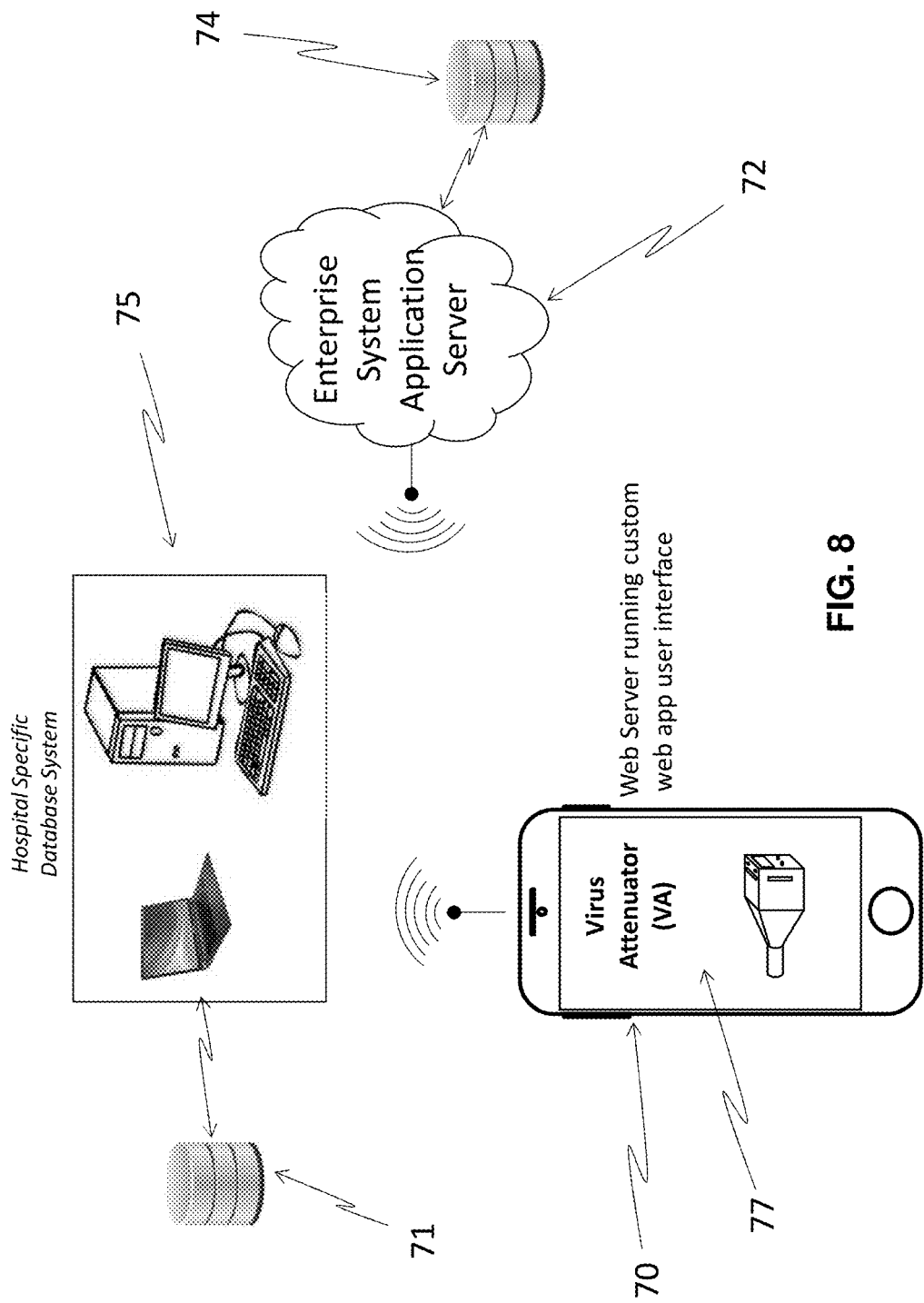
FIG. 8 shows a data collection scheme of an embodiment of a virus attenuator.

FIG. 8 depicts the virus application 77 running on a remote device, illustrated as a smart phone 70. Microcontroller 51 may be interfaced with wireless module 52 (illustrated in FIG. 6) of control board 26 and configured to transmit temperature, gas pressure, relative humidity, and carbon dioxide sensor data to virus application 77 of a remote device, e.g., smart phone 70. Virus attenuator application 70 communicates wirelessly via Bluetooth Low Energy (BLE) or wireless fidelity (WiFi) to a virus attenuator enterprise application server 72. The enterprise application server 72 utilizes enterprise application server database 74 to authenticate and log virus attenuator application 77 data streams sent wirelessly from the virus attenuator microcontroller 51. In some embodiments, enterprise application server 72 communicates with patient database 71 under provider database server 75. Application 77 may be configured to be enabled by a web-server, such as application server 72, and is configured to allow monitoring of wireless signals from virus attenuator 10.

Figure 9:
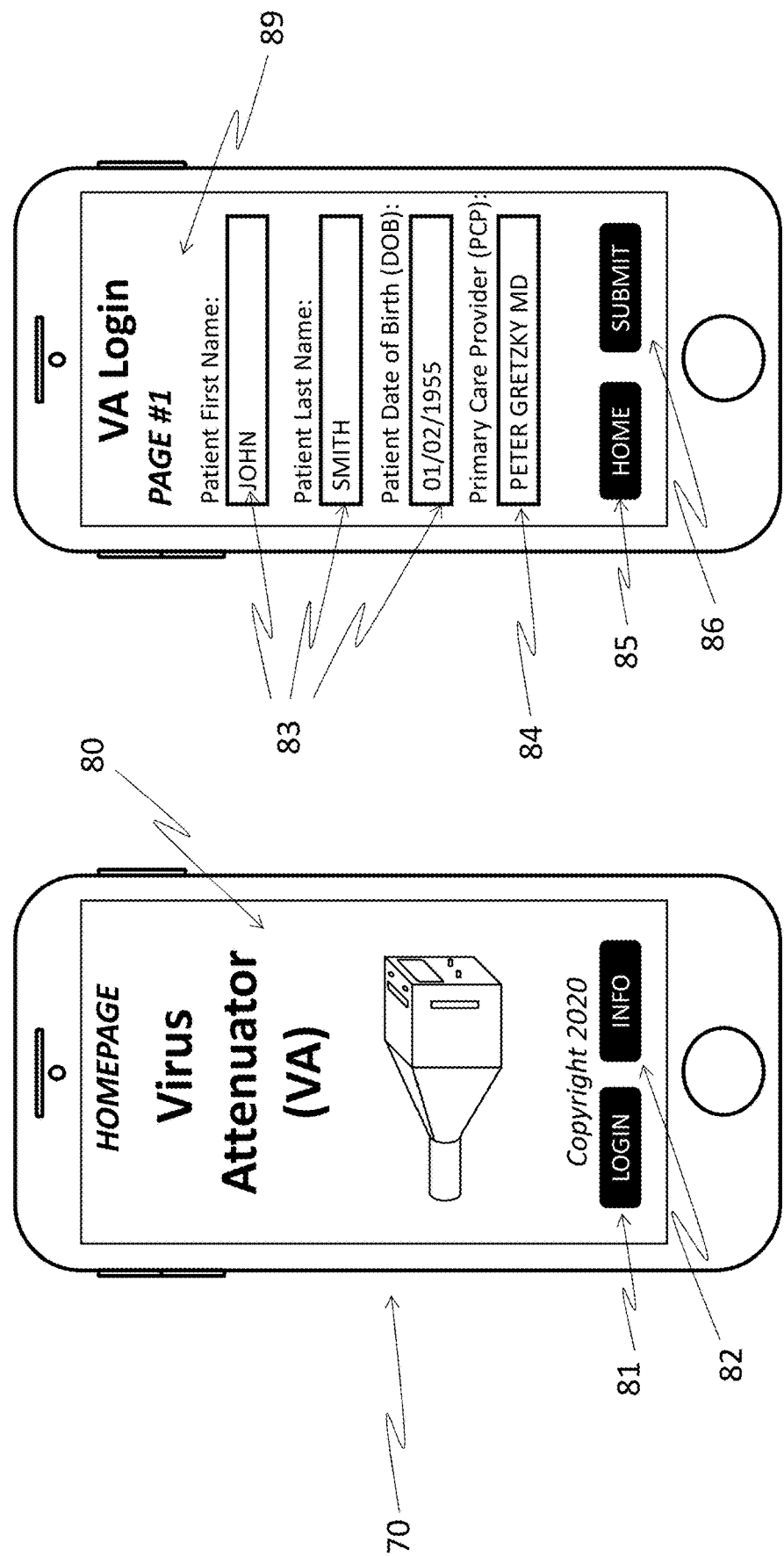
FIG. 9 shows a front view of 2 screens on a smart phone wirelessly connected to the virus attenuator application running in FIG. 8.
Figure 10:
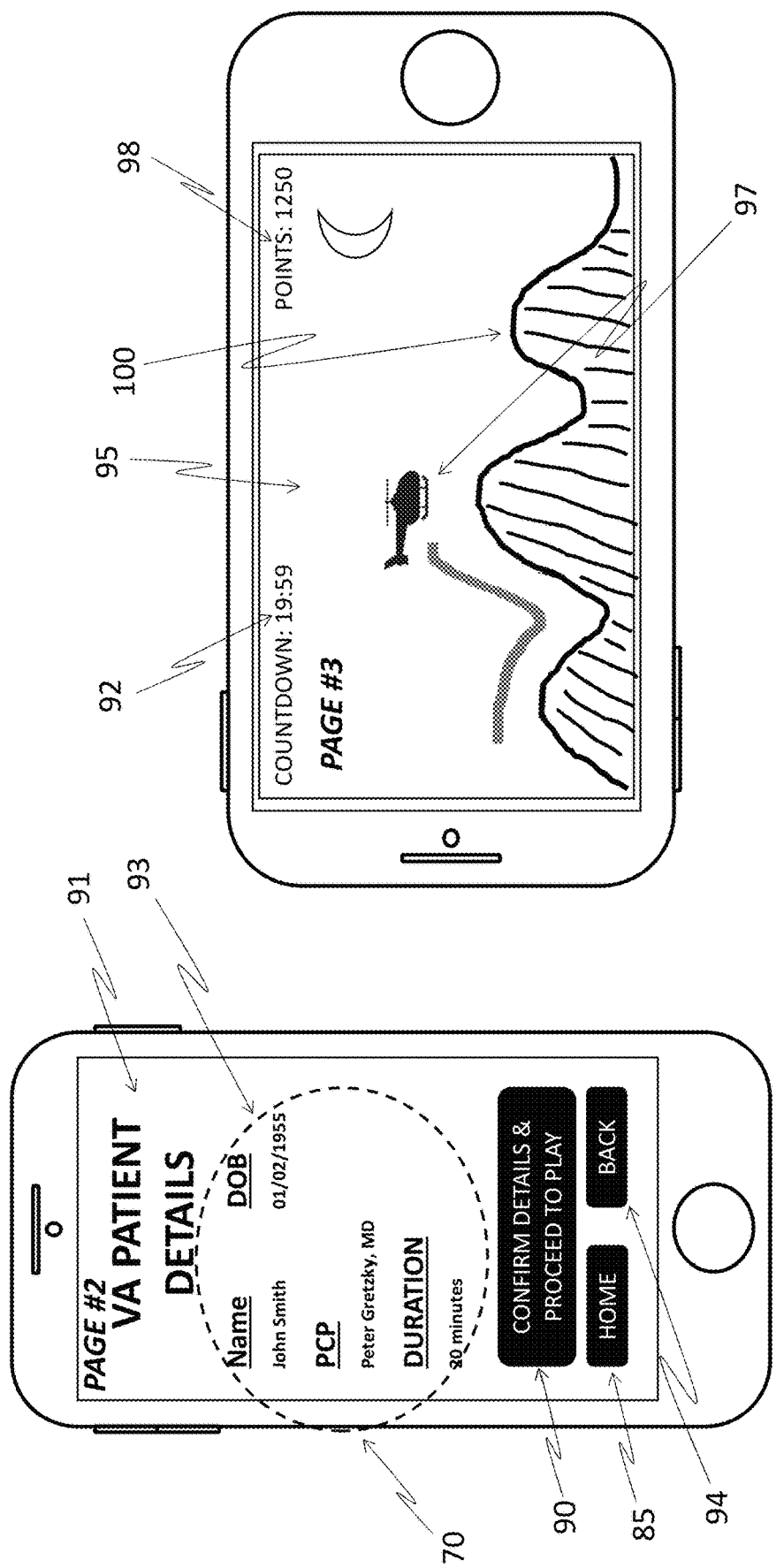
FIG. 10 shows a front view of 2 additional screens on a smart phone wirelessly connected to the virus attenuator application running in FIG. 8.
Figure 11:
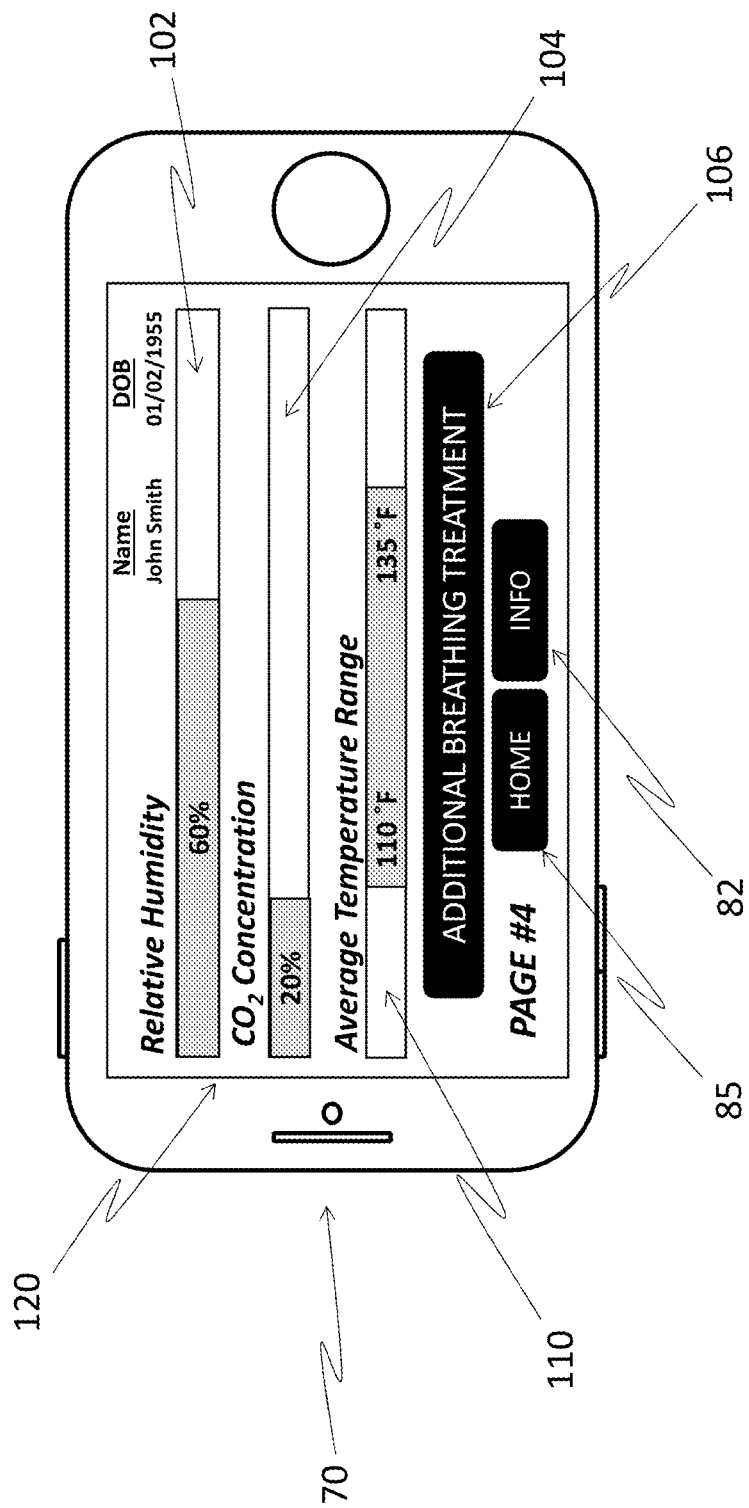
FIG. 11 shows a front view summary screen on a smart phone wirelessly connected to the virus attenuator application running in FIG. 8.

In the exemplary embodiments shown in FIG. 9, FIG. 10, and FIG. 11, various screens are depicted for the virus attenuator application 77 running on smart phone 70. In FIG. 9, the homepage 80 is shown with login touchscreen field 81 and info touchscreen field 82. Login touchscreen field 81 when selected, takes the user to virus attenuator login screen 89, with patient entry fields 83, primary care provider entry field 84, home touchscreen field 85 and submit touchscreen field 86. It is generally understood by those skilled in the art of application development that selecting patient entry field 83 and provider entry field 84 activates a keyboard screen whereby the user can enter the appropriate information. By selecting the submit touchscreen field 86, the virus attenuator application 77 brings the user to the virus attenuator patient details screen 91. Virus attenuator patient details screen 91 has patient summary fields 93, therapy duration 99, confirmation of information and proceed to play touchscreen field 90, home touchscreen field 85, and back touchscreen field 94. By user selection of the confirmation of information and proceed to play touchscreen field 90, the virus attenuator application 77 is sent to the virus attenuator (VA) game page 95. Virus attenuator game page 95 has countdown timer 92, VA game points 98, and VA flying emoji 97. In some embodiments, as microcontroller 51 is controlling the virus attenuator 10, microcontroller is transmitting temperature, pressure, humidity, and carbon dioxide signals wirelessly to virus attenuator application 77 and based on the pressure decreasing from inhalation, VA flying emoji 97 is elevated. Minimum inhalation pressure and cyclic nature of inhalation is defined by inhalation boundary curve 100. The user gains VA game points 98 by keeping the VA flying emoji 97 above the inhalation boundary curve 100. In some embodiments, inhalation boundary curve 100 is user definable and scalable, with virus application 77 collecting pressure values and automatically scaling the inhalation boundary curve 100. In this manner, the use is incentivized to maximize the VA game points 98 by maintaining the VA flying emoji 97 just above the inhalation boundary curve 100, thereby maximizing inhalation at the desired therapeutic temperature of 100° F.-140° F. for 20 minutes and reducing virus plaque forming units by up to 100x.

In some embodiments, such as the embodiment illustrated in FIG. 11, virus attenuator application summary page 120 is depicted with therapeutic humidity results 102, carbon dioxide results 104, and average temperature range 110. Additional breathing treatment touchscreen 106 is used to repeat the treatment by the user, while home touchscreen field 85 and info touchscreen field 82 are to page to various screens.

Figure 12:
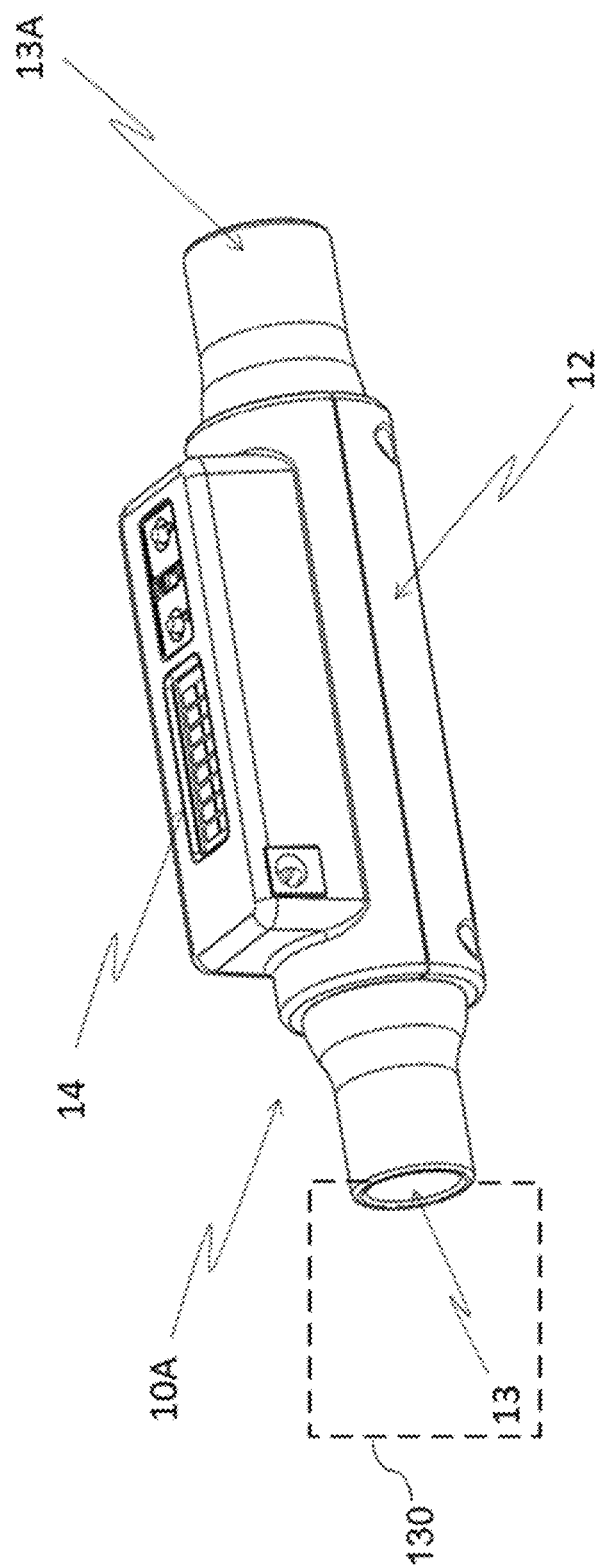
FIG. 12 shows a side perspective view of a virus attenuator intended for use in-line with a ventilator or CPAP machine according to the invention.
Figure 13:
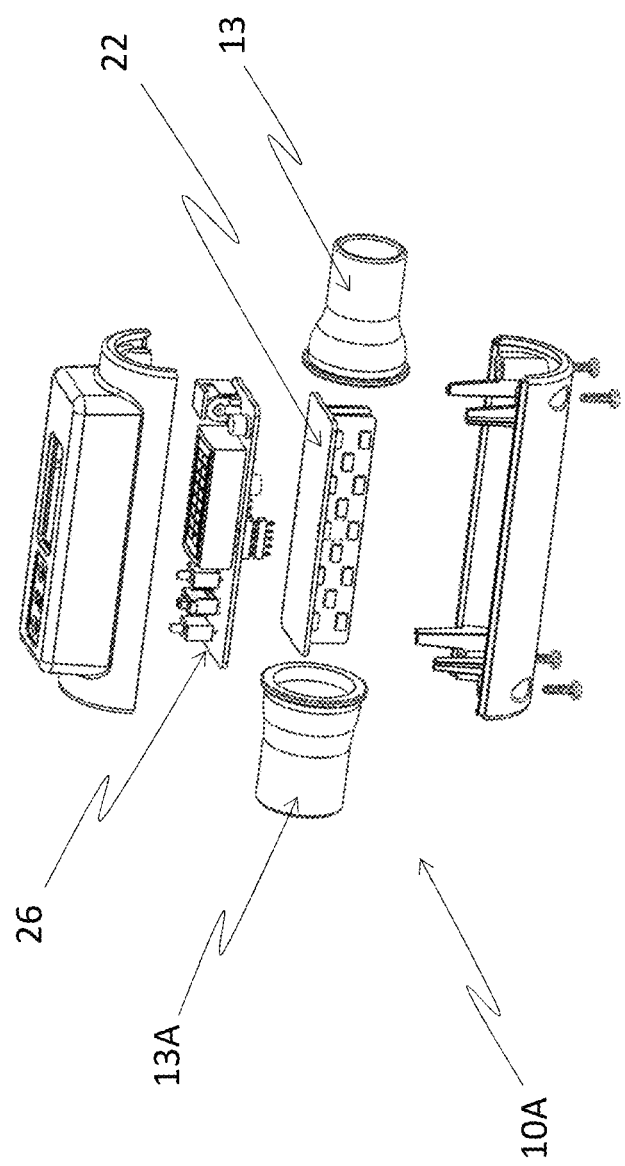
FIG. 13 shows an exploded perspective view of the virus attenuator illustrated in FIG. 12.

In some embodiments, such as the embodiment illustrated in FIG. 12, virus attenuator 10A is depicted with housing 12, gas ejection nozzle 13, and intake port 13A. Display 14 provides a user with temperature setpoint data along with real time virus attenuator gas ejection nozzle 13 gas temperature. As best shown in FIG. 13, an exploded view of in-line virus attenuator 10A depicts gas ejection nozzle 13, gas intake port 13A, control board 26 and heater board 22. In-line virus attenuator 10A is designed for an in-line application on generally available ventilators and CPAP machines which are enabled with gas pressure generating fans. In this respect, virus attenuator 10A may be part of a breathing system including virus attenuator 10A coupled to a breathing device 130, which may include a ventilator and/or a CPAP machine.

The present invention also provides a method of treating a patient infected with a respiratory virus using virus attenuator 10 and a breathing device, such as mask 2 or breathing device 130 (a ventilator and/or a CPAP machine). The method includes fitting breathing device 2, 130 to the patient so the patient breathes in gas, such as air, through breathing device 2, 130. Virus attenuator 10 is coupled to breathing device 2, 130 to form a breathing system. Heater 22 inside the interior of housing 12 of virus attenuator 10 heats contacting gas to a virus attenuating temperature. The heated gas then goes into breathing device 2, 130 through gas ejection nozzle 13 of virus attenuator 10, which is coupled to breathing device 2, 130. The heated gas from virus attenuator 10 may then be inhaled by the patient through breathing device 2, 130 to heat the upper respiratory tract of the patient. In this respect, the method includes producing heated gas that is at a virus attenuating temperature using virus attenuator 10 and providing the heated gas to the patient through breathing device 2, 130.

Figure 14:
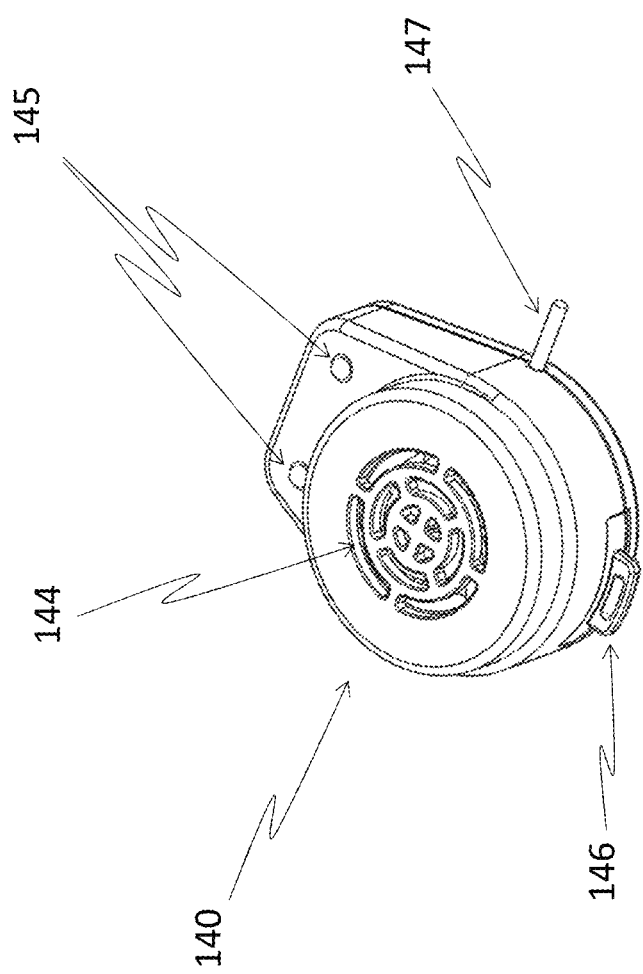
FIG. 14 shows an isometric view of an exemplary embodiment of a virus attenuator which is configured as a module that is a direct fit into a standard mask front port.
Figure 15:
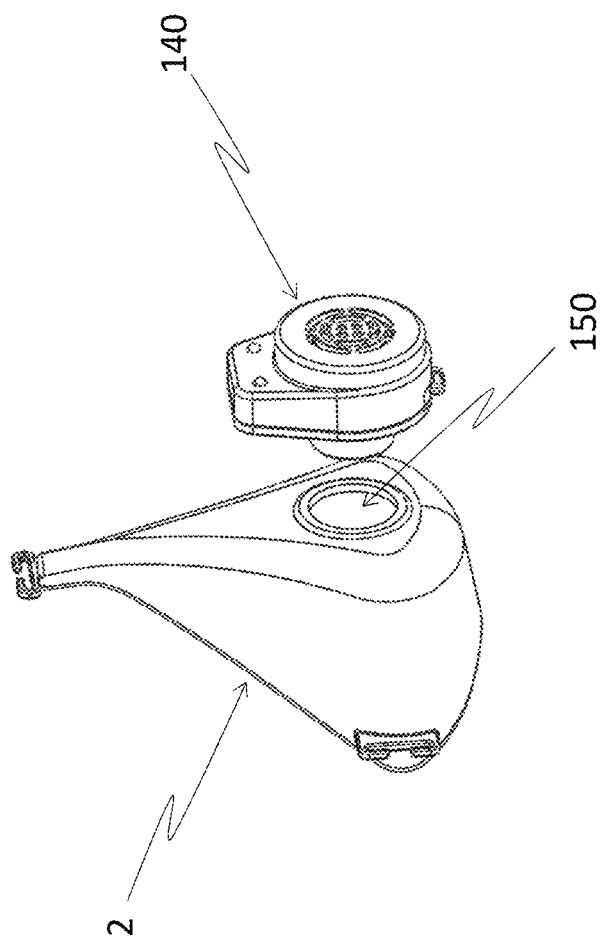
FIG. 15 shows the virus attenuator module of FIG. 14 being fitted into a standard rebreathing mask.

In some embodiments, such as the embodiment illustrated in FIG. 14, virus attenuator module 140 is shown with gas input grill 142, input power cord 147, status LEDs 145, and replaceable filter 146. As best shown in FIG. 15, virus attenuator module 140 of FIG. 14 provides a direct fit into known rebreathing mask 2 using standardized port 150, which may also be referred to as "a coupler."

Figure 16:
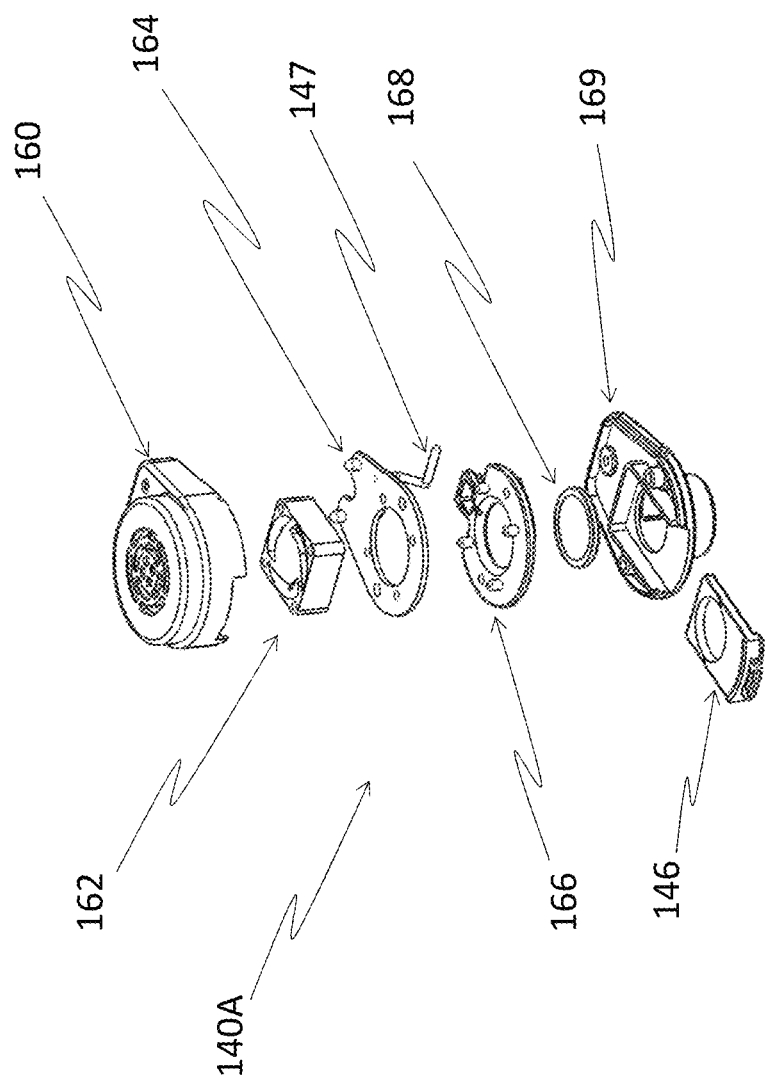
FIG. 16 shows a top right exploded view of an exemplary embodiment of a virus attenuator module with various components and configured without a heater.

Referring now to FIG. 16, it is illustrated how virus attenuator module 140A may comprise outer housing 160, inner housing 169, gas pressure producing fan 162, control board 164, filter cartridge 168, filter cartridge holder 146, power cord 147, and filter frame 166. In some embodiments, control board 164 is a singular printed circuit board housing control circuitry, heater circuitry, and sensor circuitry. In the illustrated embodiment, virus attenuator modular 140A may lack a heater and instead is configured to only output pressurized gas with a gas pressure that is greater than atmospheric pressure.

Figure 17:
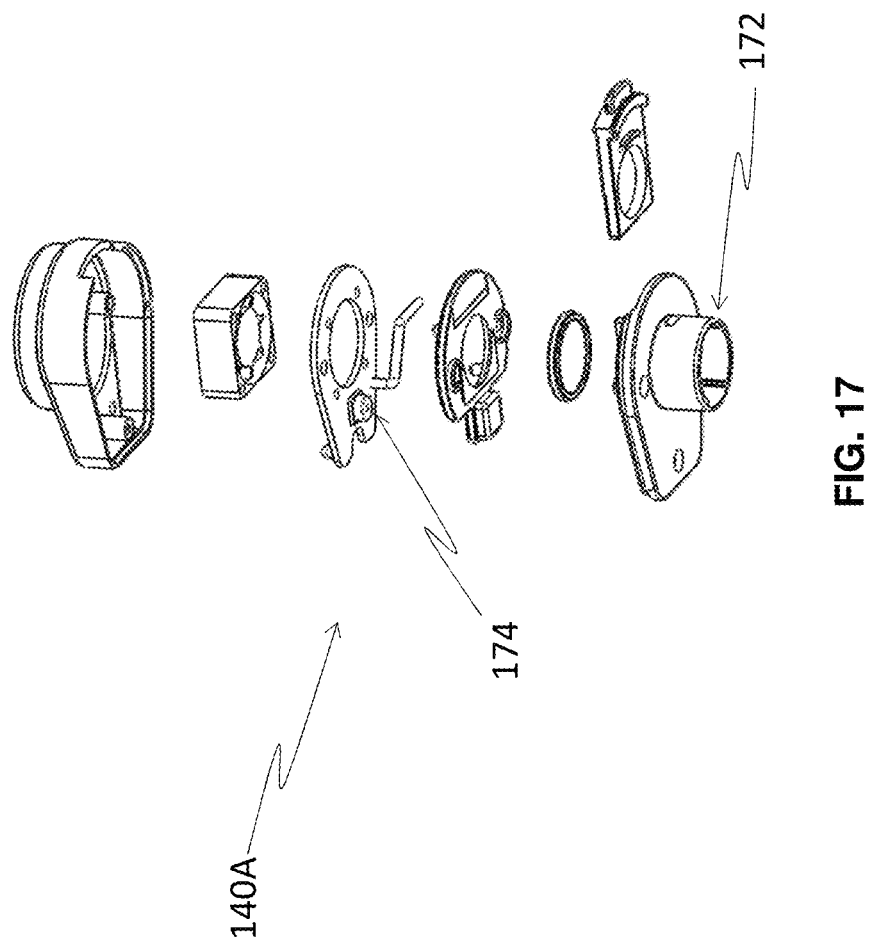
FIG. 17 shows a bottom left exploded view of an exemplary embodiment of the virus attenuator module of FIG. 16.

As best shown in FIG. 17, virus attenuator module 140A as shown in FIG. 16 has sensor block 174 comprised of pressure, humidity, and temperature sensors. Virus attenuator module 140 forces gas through output port 172 whose outside dimension is equal to the inside dimension of rebreathing mask 2 standardized port 150.

Figure 18:
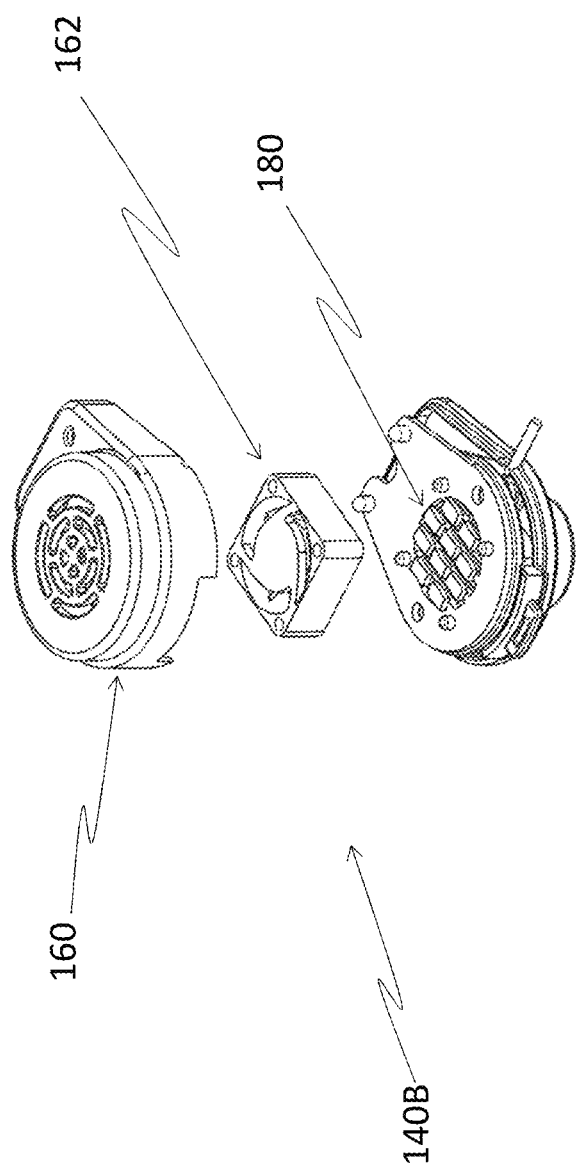
FIG. 18 shows a top right partially exploded isometric view of an exemplary embodiment of a virus attenuator module with a heater.
Figure 19:
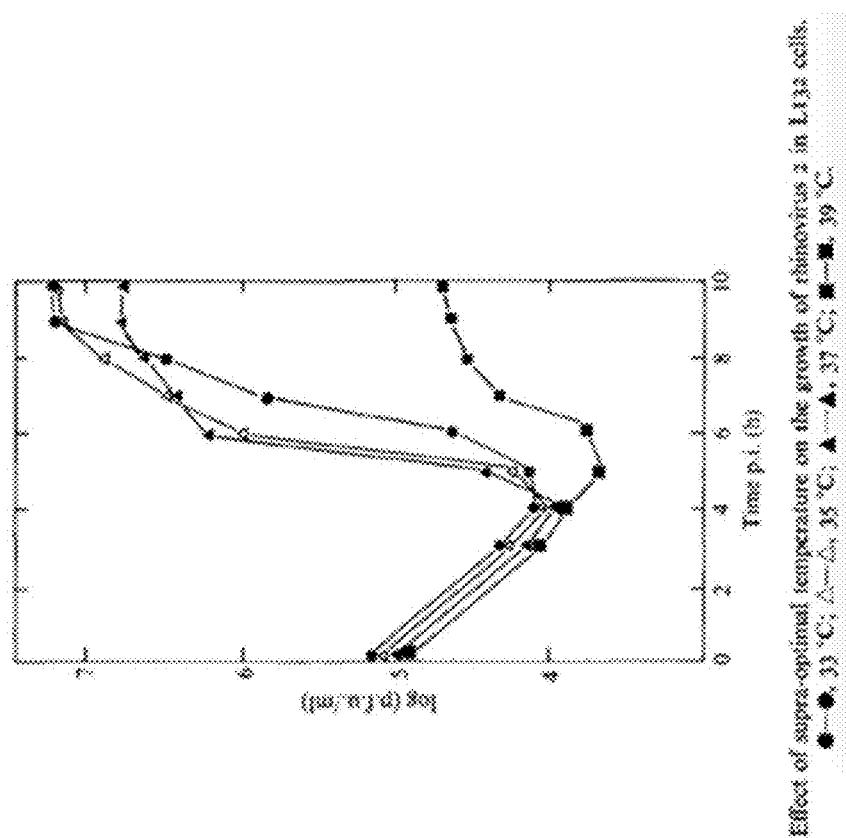
FIG. 19 shows a graph illustrating the effect of increased temperature on the growth of a rhinovirus.
Figure 20:
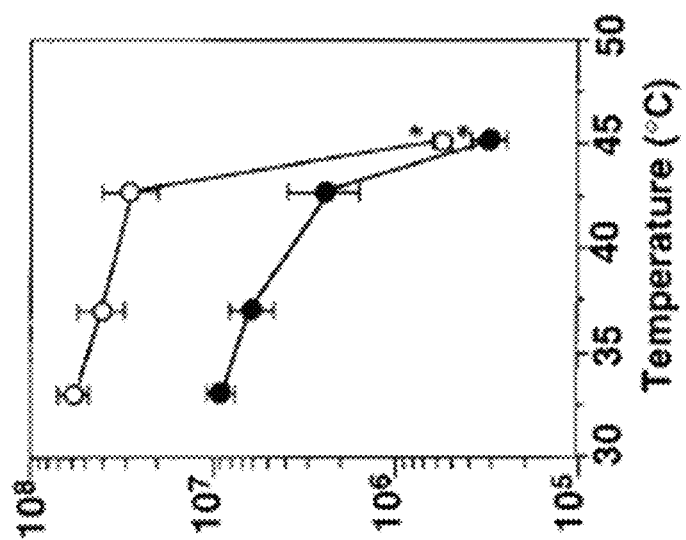
FIG. 20 shows a graph illustrating the effect of increased temperature on the growth of a virus.
Figure 21:
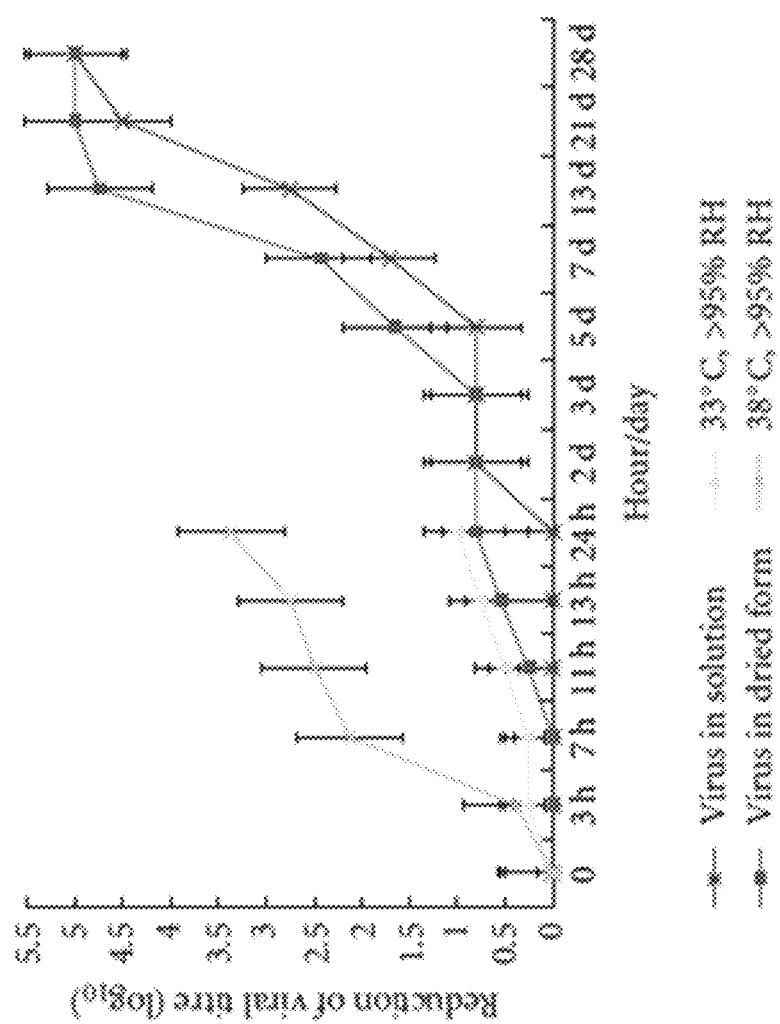
FIG. 21 shows a graph illustrating the 24-hour reduction of viral proliferation of SARS-CoV in response to an elevated temperature.

Referring now to FIG. 18, virus attenuator module 140B is shown with a plurality of surface mount resistors 180 which provides heated gas when gas producing fan 162 blows gas or a different gas over surface mount resistors 180 with voltage stimulus applied. In other respects, virus attenuator module 140B may be similar to virus attenuator module 140A.

From the foregoing, it should be appreciated that the virus attenuator provided according to the present invention can provide heated gas to a patient in order to create a localized hyperthermic environment in the URT of the patient. The local hyperthermic environment can decrease the ability of a respiratory virus to replicate, which can reduce the duration and severity of viral infection. The virus attenuator can measure many different parameters and be monitored and controlled to adjust the patient's therapy, either in-person or remotely to reduce the risk of a healthcare provider becoming infected. Thus, the virus attenuator provided according to the present invention provides a way to reduce the duration and severity of a respiratory viral infection in a manner that can reduce the risk of a healthcare provider becoming infected by the virus.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A virus attenuator, comprising:
   a housing defining an interior and having at least one intake port fluidly coupled to the interior and a gas ejection nozzle fluidly coupled to the interior, the gas ejection nozzle being configured to couple to a mask;
   at least one heater disposed in the interior between the at least one intake port and the gas ejection nozzle such that at least some gas brought into the interior through the at least one gas intake port contacts the at least one heater, the at least one heater being configured to heat contacting gas to a virus attenuating temperature before the contacting gas exits the interior through the gas ejection nozzle, the at least one heater comprising a heater board including a surface and a plurality of slots formed in the surface such that all gas flowing through the at least one intake port and the gas ejection nozzle passes through at least one of the slots before exiting the interior through the gas ejection nozzle;
   a gas pressure producing fan disposed in the interior and configured to produce a gas flow directed at the at least one heater, wherein the fan rotates about a fan axis that extends through the gas ejection nozzle without extending through the at least one intake port;
   a control board comprising a microcontroller disposed in the interior; and
   a sensor board comprising a carbon dioxide sensor operably coupled to the microcontroller.

2. The virus attenuator of claim 1, wherein the fan is configured to produce pressurized gas with a pressure of between 80 mm Hg and 100 mm Hg.

3. The virus attenuator of claim 1, wherein the microcontroller is configured to control a heater board power supplied to the heater board and a fan speed of the fan using pulse width modulation.

4. The virus attenuator of claim 1, wherein the sensor board further comprises a temperature sensor operably coupled to the microcontroller, a pressure sensor operably coupled to the microcontroller, and a humidity sensor operably coupled to the microcontroller.

5. The virus attenuator of claim 4, wherein the microcontroller is configured to determine a heater board temperature, determine an exhaust gas temperature, determine a relative humidity, determine a gas pressure, and determine a carbon dioxide content based on received signals from the temperature sensor, the pressure sensor, the humidity sensor, and the carbon dioxide sensor.

6. The virus attenuator of claim 5, wherein the temperature sensor comprises a thermistor in a resistor divider network.

7. The virus attenuator of claim 4, wherein the microcontroller is interfaced with a wireless module and is configured to transmit temperature, gas pressure, relative humidity, and carbon dioxide sensor data to an application of a remote device.

8. The virus attenuator of claim 7, wherein the application is configured to be enabled from a web-server and is configured to allow monitoring of wireless signals from the virus attenuator.

9. The virus attenuator of claim 1, wherein the control board comprises:
   a fan driver;
   a heater driver;
   a display, the display comprising a light-emitting diode (LED) display or a liquid-crystal display;
   a wireless module; and
   indicator lamps configured to indicate therapeutic range achievement.

10. The virus attenuator of claim 1, wherein the heater board comprises a plurality of resistors mounted to the surface and the slots are disposed alternately between the resistors.

11. The virus attenuator of claim 1, wherein the fan is configured to produce a static pressure of 10 mmHg to 150 mmHg.

12. The virus attenuator of claim 1, wherein the gas ejection nozzle is part of a tapered exhaust output that is configured to fit a rebreathing mask with a diameter of 0.65 inches to 0.75 inches.

13. The virus attenuator of claim 1, wherein the gas ejection nozzle is part of a tapered exhaust output configured to fit a plurality of adapters configured to couple the tapered exhaust output to a rebreathing mask.

14. The virus attenuator of claim 1, wherein the virus attenuating temperature is between 100° F. and 140° F.

15. The virus attenuator of claim 1, wherein the virus attenuating temperature is between 98° F. and 140° F.

16. The virus attenuator of claim 1, wherein the housing is configured to adapt into a ventilator breathing circuit or a continuous positive airway pressure (CPAP) breathing circuit.

17. A breathing system, comprising:
   a mask comprising a coupler; and
   a virus attenuator coupled to the mask, the virus attenuator comprising:
      a housing defining an interior and having at least one intake port fluidly coupled to the interior and a gas ejection nozzle fluidly coupled to the interior and coupled to the coupler of the mask;
      at least one heater disposed in the interior between the at least one intake port and the gas ejection nozzle such that at least some gas brought into the interior through the at least one gas intake port contacts the at least one heater, the at least one heater being configured to heat contacting gas to a virus attenuating temperature before the contacting gas exits the interior through the gas ejection nozzle into the mask, the at least one heater comprising a heater board including a surface and a plurality of slots formed in the surface such that all gas flowing through the at least one intake port and the gas ejection nozzle passes through at least one of the slots before exiting the interior through the gas ejection nozzle;
      a gas pressure producing fan disposed in the interior and configured to produce a gas flow directed at the at least one heater, wherein the fan rotates about a fan axis that extends through the gas ejection nozzle without extending through the at least one intake port;
      a control board comprising a microcontroller disposed in the interior; and
      a sensor board comprising a carbon dioxide sensor operably coupled to the microcontroller.

18. A method of treating a patient infected with a respiratory virus, the method comprising:
   fitting a breathing device to the patient so the patient breathes in gas through the breathing device;
   producing heated gas that is at a virus attenuating temperature using a virus attenuator, the virus attenuator comprising:
      a housing defining an interior and having at least one intake port fluidly coupled to the interior and a gas ejection nozzle fluidly coupled to the interior, the gas ejection nozzle being coupled to a coupler of the breathing device;

at least one heater disposed in the interior between the at least one intake port and the gas ejection nozzle such that at least some gas brought into the interior through the at least one gas intake port contacts the at least one heater, the at least one heater heating contacting gas to the virus attenuating temperature to produce the heated gas, the at least one heater comprising a heater board including a surface and a plurality of slots formed in the surface such that all gas flowing through the at least one intake port and the gas ejection nozzle passes through at least one of the slots before exiting the interior as the heated gas through the gas ejection nozzle;

a gas pressure producing fan disposed in the interior and configured to produce a gas flow directed at the at least one heater, wherein the fan rotates about a fan axis that extends through the gas ejection nozzle without extending through the at least one intake port;

a control board comprising a microcontroller disposed in the interior; and a sensor board comprising a carbon dioxide sensor operably coupled to the microcontroller; and providing the heated gas to the patient through the breathing device.

\* \* \* \* \*